United States Patent
Holley et al.

(10) Patent No.: US 9,597,479 B2
(45) Date of Patent: Mar. 21, 2017

(54) METHOD AND APPARATUS FOR TREATMENT OF SLEEP DISORDERS

(75) Inventors: Liam Holley, Marrickville (AU); Jeffrey Peter Armitstead, North Sydney (AU); Steven Paul Farrugia, Lugarno (AU); Dinesh Ramanan, Telopea (AU); Pallavi Gosain, Merrylands (AU)

(73) Assignee: RedMed Limited (AU)

( * ) Notice: Subject to any disclaimer, the term of this patent is extended or adjusted under 35 U.S.C. 154(b) by 121 days.

(21) Appl. No.: 13/984,398

(22) PCT Filed: Feb. 10, 2012

(86) PCT No.: PCT/AU2012/000133
§ 371 (c)(1),
(2), (4) Date: Aug. 8, 2013

(87) PCT Pub. No.: WO2012/106775
PCT Pub. Date: Aug. 16, 2012

(65) Prior Publication Data
US 2013/0324788 A1    Dec. 5, 2013

(30) Foreign Application Priority Data
Feb. 11, 2011   (AU) ................. 2011900446

(51) Int. Cl.
*A61M 21/02* (2006.01)
*A61B 5/087* (2006.01)
(Continued)

(52) U.S. Cl.
CPC ............. *A61M 21/02* (2013.01); *A61B 5/087* (2013.01); *A61B 5/4809* (2013.01);
(Continued)

(58) Field of Classification Search
CPC .......... A61M 21/00; A61M 2021/0016; A61M 2021/0044; A61M 2021/0083;
(Continued)

(56) References Cited

U.S. PATENT DOCUMENTS 5,008,865 A * 4/1991 Shaffer et al. .................. 368/10
6,126,294 A 10/2000 Koyama et al.
(Continued)

FOREIGN PATENT DOCUMENTS

JP  2011027622 A  2/2011
WO  WO 8908476 A1 * 9/1989 ............ A61M 21/00
(Continued)

OTHER PUBLICATIONS

Written Opinion of the International Preliminary Examining Authority for Application No. PCT/AU2012/000133 dated Jan. 11, 2013.
(Continued)

*Primary Examiner* — Charles A Marmor, II
*Assistant Examiner* — Thaddeus Cox
(74) *Attorney, Agent, or Firm* — Lerner, David, Littenberg, Krumholz & Mentlik, LLP

(57) ABSTRACT

A system for therapy may include a mask (200) for a patient having a frame, cushion, forehead support and a light (100). The mask is connectable to a respiratory treatment apparatus, such as a flow generator, to receive breathable gas for a respiratory therapy. The light may also be connected to the power system and/or control system of the apparatus. A light may also be included in a module, such as a docking station, for a respiratory treatment apparatus. The lights may be controlled by one or more processors, and may be responsive to detected conditions, to assist with therapy. For example, the light may be turned on at a predetermined time or may be synchronized with the patient's sleep state, to
(Continued)

assist in waking up the patient or re-setting the patient's circadian rhythm. Other components, such as sound and aroma generators of the system, may also be controlled for such therapies.

50 Claims, 6 Drawing Sheets

(51) Int. Cl.
| | |
|---|---|
| *A61M 16/06* | (2006.01) |
| *A61N 5/06* | (2006.01) |
| *A61B 5/00* | (2006.01) |
| *A61M 16/00* | (2006.01) |
| *A61M 16/10* | (2006.01) |
| *A61M 21/00* | (2006.01) |

(52) U.S. Cl.
CPC .... *A61M 16/0057* (2013.01); *A61M 16/0066* (2013.01); *A61M 16/06* (2013.01); *A61M 16/10* (2013.01); *A61N 5/06* (2013.01); *A61N 5/0618* (2013.01); *A61M 16/0683* (2013.01); *A61M 2016/0027* (2013.01); *A61M 2016/0039* (2013.01); *A61M 2021/0016* (2013.01); *A61M 2021/0027* (2013.01); *A61M 2021/0044* (2013.01); *A61M 2205/3375* (2013.01); *A61M 2205/3561* (2013.01); *A61M 2205/3584* (2013.01); *A61M 2205/3592* (2013.01); *A61M 2205/502* (2013.01); *A61M 2205/8206* (2013.01); *A61M 2209/086* (2013.01); *A61N 2005/0648* (2013.01)

(58) Field of Classification Search
CPC .. A61M 16/06–16/0694; A61B 4/4818; A61B 5/4809; A61N 5/06; A61N 2005/0647–2005/0648
See application file for complete search history.

(56) References Cited

U.S. PATENT DOCUMENTS

| | | | |
|---|---|---|---|
| 2003/0062856 A1 | 4/2003 | Yano et al. | |
| 2004/0163648 A1 | 8/2004 | Burton | |
| 2004/0225340 A1 | 11/2004 | Evans | |
| 2006/0030907 A1 | 2/2006 | McNew | |
| 2007/0118026 A1* | 5/2007 | Kameyama et al. | 600/300 |
| 2008/0123332 A1* | 5/2008 | Searfoss | A61B 5/00 362/231 |
| 2008/0216835 A1* | 9/2008 | McGinnis | A61M 16/00 128/204.23 |
| 2009/0203972 A1 | 8/2009 | Heneghan et al. | |
| 2010/0076253 A1* | 3/2010 | Altman | A61M 21/00 600/28 |
| 2011/0015468 A1 | 1/2011 | Aarts et al. | |
| 2011/0056493 A1* | 3/2011 | Miller et al. | 128/203.16 |
| 2011/0257712 A1* | 10/2011 | Wells et al. | 607/90 |
| 2012/0227742 A1* | 9/2012 | Witt et al. | 128/205.24 |

FOREIGN PATENT DOCUMENTS

| | | |
|---|---|---|
| WO | 2006109969 A1 | 10/2006 |
| WO | 2009073817 A1 | 6/2009 |
| WO | 2010033429 A1 | 3/2010 |
| WO | 2010076707 A1 | 7/2010 |
| WO | 2011006199 A1 | 1/2011 |

OTHER PUBLICATIONS

International Search Report for Application No. PCT/AU2012/000133 dated May 14, 2012.
Written Opinion of the International Preliminary Examining Authority for Application No. PCT/US2012/000133 dated Apr. 3, 2013.
Supplementary European Search Report for Application No. 12744691.2 dated Mar. 1, 2016.
Extended European Search Report for Application No. EP12744691 dated Jun. 13, 2016.

\* cited by examiner

METHOD AND APPARATUS FOR TREATMENT OF SLEEP DISORDERS

CROSS REFERENCE TO RELATED APPLICATIONS

This application is a national phase entry under 35 U.S.C. §371 of International Application No. PCT/AU2012/000133 filed Feb. 10, 2012, published in English, which claims priority from Australia Provisional Patent Application No. 2011900446 filed Feb. 11, 2011, all of which are hereby incorporated herein by reference.

FIELD OF THE TECHNOLOGY

The present disclosure relates to systems, methods, and apparatus for treatment of sleep disorders.

SUMMARY OF THE TECHNOLOGY

One aspect of the present technology relates to a device for treating a sleep disorder.

Another aspect of the present technology relates to a method for treating a sleep disorder.

Another aspect of the present technology relates to an apparatus for treating a sleep disorder.

Another aspect of the present technology relates to an apparatus for treating a sleep disorder comprising a light.

Another aspect of the present technology relates to a method for treating a sleep disorder with light.

Another aspect of the present technology relates to a respiratory therapy system with a light.

Another aspect of the present technology relates to a flow generator with a light.

Another aspect of the present technology relates to a mask system with a light.

Another aspect of the present technology relates to a respiratory therapy system comprising a control system and a light, the control system adapted to control illumination of the light to facilitate transition of the patient between a sleep state and an awake state.

Another aspect of the present technology relates to a mask system comprising a light attached thereto proximate the patient's eyes.

Another aspect of the present technology relates to mask system with a light attached thereto to direct the light in a downward trajectory towards the patient's eyes.

Another aspect of the present technology relates to a mask system with a light, the light being adapted to connect to a frame of the mask system.

Another aspect of the present technology relates to a mask system with a light, the light being adapted to connect to a forehead support of the mask system.

Another aspect of the present technology relates to a respiratory therapy system with a light, the light being activated at a pre-determined time.

Another aspect of the present technology relates to a respiratory therapy system with a light, the light being activated at a time set by the patient.

Another aspect of the present technology relates to a respiratory therapy system with a light, the light being activated at a time calculated by the flow generator.

Another aspect of the present technology relates to a respiratory therapy system with a light, the light being activated at a time calculated by the flow generator based on the start time of the patient's therapy.

Another aspect of the present technology relates to a respiratory therapy system with a light, the light being activated at a time calculated by the flow generator based on the required duration of the patient's respiratory therapy.

Another aspect of the present technology relates to a respiratory therapy system with a light, activation of the light being triggered by a detection of the patient's sleep state.

Another aspect of the present technology relates to a respiratory therapy system with a light and a flow generator, the flow generator estimating the patient's sleep state and activation of the light being triggered by the patient's sleep state.

Another aspect of the present technology relates to a respiratory therapy system with a light and a flow generator, the flow generator may transmit a signal to a processor to indicate the patient's sleep state, and the processor may then transmit a signal to turn the light on or off.

Another aspect of the present technology relates to a respiratory therapy system with a light, the brightness of the light transitioning progressively between an off state and an on state.

Another aspect of the present technology relates to a respiratory therapy system with a light and a flow generator, the light being adapted to synchronize with a patient's sleep state and the flow generator computing the patient's sleep state. The brightness of the light may be synchronized with the patient's sleep state.

Another aspect of the present technology relates to a respiratory therapy device for treating seasonal affective disorder ("SAD").

Another aspect of the present technology relates to a respiratory therapy device for treating Circadian Rhythm Sleep Disorder ("CRSD").

Another aspect of the present technology relates to a method of treating a sleep disorder, comprising measuring a patient respiratory characteristic and modifying a parameter of a light therapy device based on the patient respiratory characteristic.

Another aspect of the present technology relates to a method of treating a sleep disorder, comprising delivering a light therapy to a patient and measuring a patient response to the light therapy, modifying a parameter of a respiratory therapy device based on the patient response to the light therapy.

In some embodiments of the technology, a device is constructed and arranged to provide positive pressure therapy and phototherapy to a person.

For example, a respiratory therapy system for treating a patient with a sleep disorder may include a mask adapted to sealingly engage with a patient. The system may also include a flow generator adapted to deliver pressurized breathable gas to the mask. A therapy light having an off state and an on state may also be included in the system. The therapy light may be in electrical communication with the flow generator, and the flow generator may be configured to switch the light between the off state to the on state if the flow generator detects a condition, such as a predetermined time or sleep state. Such a predetermined time may be an input from a user. Such a sleep state may be an awake state.

In some such examples, the light may be controlled to gradually adjust from an off state to an on state when the patient is transitioning from sleep state to awake state. Still further the light may be controlled to gradually adjust from an on state to an off state when the patient is transitioning from awake to sleep state.

Optionally, the therapy light may be coupled at a portion of the mask. In some cases, the system may also include an aroma chamber. In some such cases, a flow generator or controller of the flow generator may be configured to selectively activate gas flow through the aroma chamber to selectively release an aroma from the chamber to a breathable gas of the mask. Optionally, the aroma chamber may be configured to include a replaceable aroma cartridge.

In some embodiments of the technology, a method may be implemented to treat a sleep disorder. The method may involve measuring at least one patient respiratory characteristic. The method may also involve sending patient respiratory characteristics to a processor. It may also involve determining the patient's sleep state as awake or asleep at the processor. It may also involve sending a signal from the processor to activate the light if the patient's sleep state is awake.

In some cases, the method may also involve sending a signal from the processor to deactivate the light based on the patient's sleep state. The method may also involve controlling the light with the processor to gradually decrease light intensity over a preset period of time. The method may also involve controlling the light with the processor to gradually increase light intensity over a preset period of time. Still further, the method may also involve controlling the light with the processor to provide a generally constant therapy intensity during a preset period of time. Moreover, the method may also involve sending a signal from the processor to activate an aroma chamber that contains an aroma, to thereby release an aroma to a breathable gas.

In some embodiments of the present technology, a mask may be implemented for use in treating a sleep disorder. The mask may include a frame, a cushion, and a light, such as one or more located on the frame. The light may be configured, such as with a controller, to switch state upon receipt of a signal from a flow generator.

In some embodiments of the present technology, a respiratory therapy system may be configured for treating sleep disordered breathing. The system may include a mask adapted to sealingly engage with the patient, a flow generator in sealing communication with the mask, a light located on one of the mask or the flow generator, and a controller, including at least one processor. The controller may be configured to set a respiratory therapy operation of the flow generator, and the controller may be further configured to set a light therapy operation of the light.

In some embodiments of the technology, a method of treating a sleep disorder in a patient may involve monitoring a person to detect a respiratory condition of a person, such as with a processor, providing a phototherapy device to the person, and controlling a change to, or changing, such as with a processor, a state of the phototherapy device upon detection of the respiratory condition.

In some embodiments of the technology, a system for treating a sleep disorder includes a light therapy module. The light therapy module may include a noncontact physiological sensor for detecting a condition of a patient. The module may also include a first interface for data communication with a mobile computing device. The module may also include a therapy light for providing a therapy to a patient. The module may also include at least one processor coupled with the sensor, the light and the first contact interface, wherein the processor is configured to set a therapy operation of the light.

In some such cases, the light therapy module may include a docking station. The docking station may have a stand, such as a receptacle, for a mobile computing device when the mobile computing device is coupled with the first interface. In some cases, the docking station may include a respiratory treatment apparatus interface for communication with a control system of a respiratory treatment apparatus. The respiratory treatment apparatus may be connectable to the docking station by an external input port located on the docking station. In some cases, a processor of the docking station, the mobile computing device or the respiratory treatment apparatus may be configured to detect a respiratory characteristic with the sensor. In some cases, a processor of the docking station, the mobile computing device or the respiratory treatment apparatus may be configured to compare respiratory characteristics detected with the sensor and detected with a sensor of the respiratory treatment apparatus.

Optionally, the light therapy module may also include a light sensor. In some such cases, a processor of the system may detect a level of light and control a change of an intensity of the light in response to light detected by the sensor. Optionally, the light therapy module may include a sound sensor and a speaker. In some such cases, a processor of the system may detect a level of sound and control a generation of a sound signal in response to sound detected by the sensor. Sound generated may include white noise. Optionally, the sound signal may include an inverse signal of the detected sound.

Other aspects, features, and advantages of the present technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various example embodiments of the technology. In such drawings.

DETAILED DESCRIPTION

The following description is provided in relation to several examples which may share common characteristics and features. It is to be understood that one or more features of any one example may be combinable with one or more features of the other examples. In addition, any single feature or combination of features in any of the example or examples may constitute an additional feature which applicants may opt to independently protect.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. The respiratory therapy devices or blowers described herein may be designed to pump fluids other than air.

Mask System

An example mask system may be any type of mask (also referred to as patient interfaces or mask systems), including nasal masks, nose & mouth masks, full-face masks and nasal prongs, pillows, nozzles & cannulae.

A mask system may include a frame, a cushion and a headgear. The frame may anchor the cushion in position and allow for attachment of headgear. The frame may be a rigid or semi rigid component. The cushion may seal with the face of the patient in order to provide therapy to the patient. The cushion may be a flexible element. The headgear may stabilize and support the frame and cushion in position on the patient's face when in use. The headgear may be a flexible or semi rigid element constructed of, for example, fabric.

Figure 1:
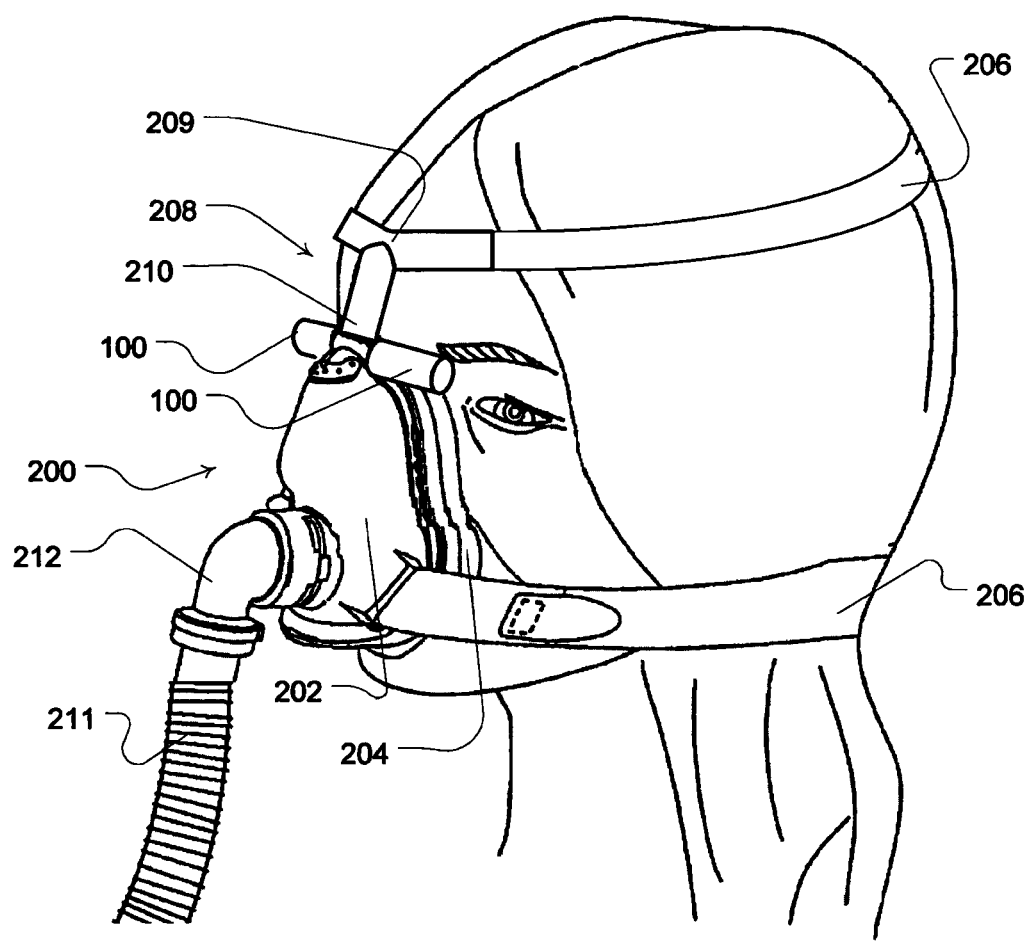
FIG. 1 is a perspective view illustrating a mask with a light on a patient according to the present technology.

FIG. 1 illustrates a mask system 200. The mask system 200 includes a frame 202, a cushion 204 and headgear 206. The frame 202 anchors the cushion 204 in position. The frame 202 may be a rigid or semi rigid component constructed of, for example, polycarbonate. The cushion 204 may be a flexible element constructed of, for example, silicone to provide a comfortable fit to the patient.

The mask system 200 may include a forehead support 208, and an elbow 212. The forehead support 208 may include a beam 210 and a forehead pad 209. The beam 210 may extend between the frame 202 and the forehead pad 209. The forehead pad may rest on the patient's forehead and receive at least one headgear strap 206. The elbow 212 includes a first end that interfaces with an aperture in the frame 202, and a second end adapted to connect to an air delivery tube 211 that delivers pressurized breathable gas to the patient (in the range of 2-40 cm $H_2O$, approximately 8-12 cm $H_2O$ for OSA treatment).

The headgear 206 is adapted to secure and stabilize the mask system 200 to the face of the patient. The headgear 206 may connect to the frame 202 and/or forehead pad 209 via an attachment means such as clips, loops or other attachment means.

Light

In FIG. 1, lights 100 are implemented with the mask system 200. The lights may include lasers, light-emitting diodes, fluorescent lamps, dichroic lamps or very bright, full-spectrum lights etc. The lights 100 may include an attachment component to secure the lights 100 to the mask system 200. For example, attachment component may include clips, adhesive, or other device and may be implemented to permit a releasable attachment of the lights. Lights 100 may be attached to an intermediate connecting element such as a flexible wire or clip body, and the intermediate element or body may attach to the mask system 200. Alternatively, lights 100 may be integrally formed with the mask system. In some such mask implemented cases, the light source of the lights 100 may be located within several inches of a user's eyes and may be no further than a distance of about five inches.

For example, lights 100 may be attached or integrally formed with forehead support 208. Forehead support 208 may be positioned proximate the patient's eyes. Lights 100 may be attached or integrally formed with beam 210. Alternatively, lights 100 may be attached or integrally formed with forehead pads 209. For example, lights 100 may be embedded or otherwise attached in the forehead pads 209.

Lights 100 may be positioned proximate to the patient's eyes. Lights 100 may be positioned proximate to one or both of the patient's eyes.

According to one aspect of the technology, lights 100 may be positioned to present the light in a downwards trajectory over the patient's eyes. Additionally, a light chamber may be formed so as to reflect and/or direct rays from an included bulb or emitter in a direction approximately parallel to the mask user's face and may also serve as a shield to prevent directing light rays where it is not desired. Advantageously, these may serve to avoid shining the lights directly into the user's eyes.

The distance from the lights 100 to the patient's eyes may be determined by the brightness of the light delivered from lights 100. For example, lights with a higher lux value may be positioned further from the patient's eyes than lights with a lower lux value.

Advantageously, if the lights are positioned close to the eyes, a light with a lower lux value may be sufficient and may also require less power to operate.

Alternatively, the lights 100 or the light chamber may be movable or adjustable such that the patient can position the lights or chamber in a desired position so as to direct or shield the light as desired. For example, the lights 100 may be attached to a malleable wire.

Figure 4:
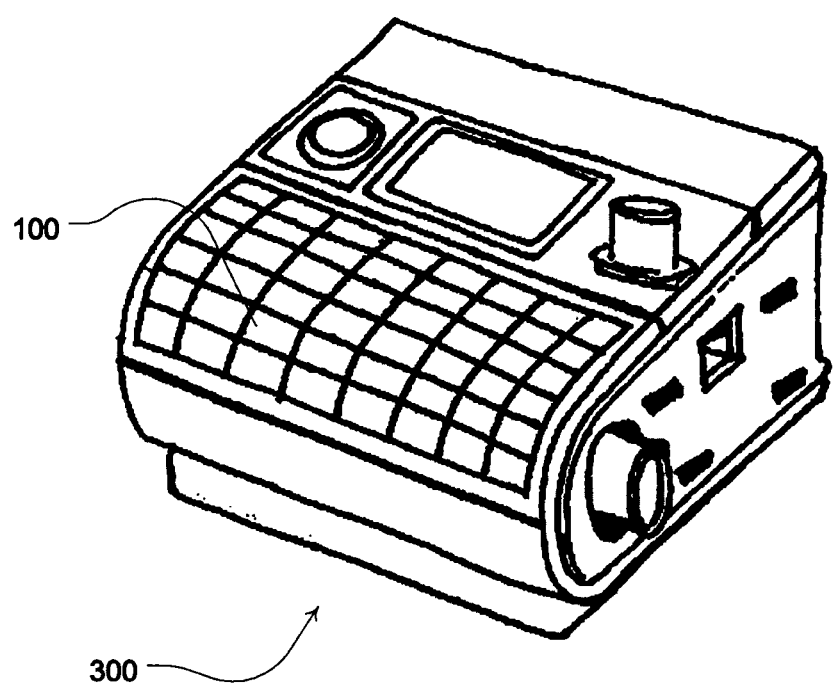
FIG. 4 is a perspective view illustrating a flow generator with a light according to the present technology.

Optionally, lights 100 may also be removably attachable or integrally formed with the flow generator or ventilator. See for example FIG. 4.

In some embodiments, lights 100 may include one or more LEDs. Optionally, the lights 100 may be configured to emit a blue wavelength. Blue LED lights may be advantageous as they may suppress melatonin secretion more than other lights, as the eyes are more sensitive to blue wavelengths. In an alternative, the lights 100 may be configured to emit green, red or blue-green wavelengths. In a further alternative, lights 100 may be configured to emit white light. In a further alternative, lights 100 may be configured to emit infrared light. Such lights may be less disturbing than other lights.

Control

Figure 2:
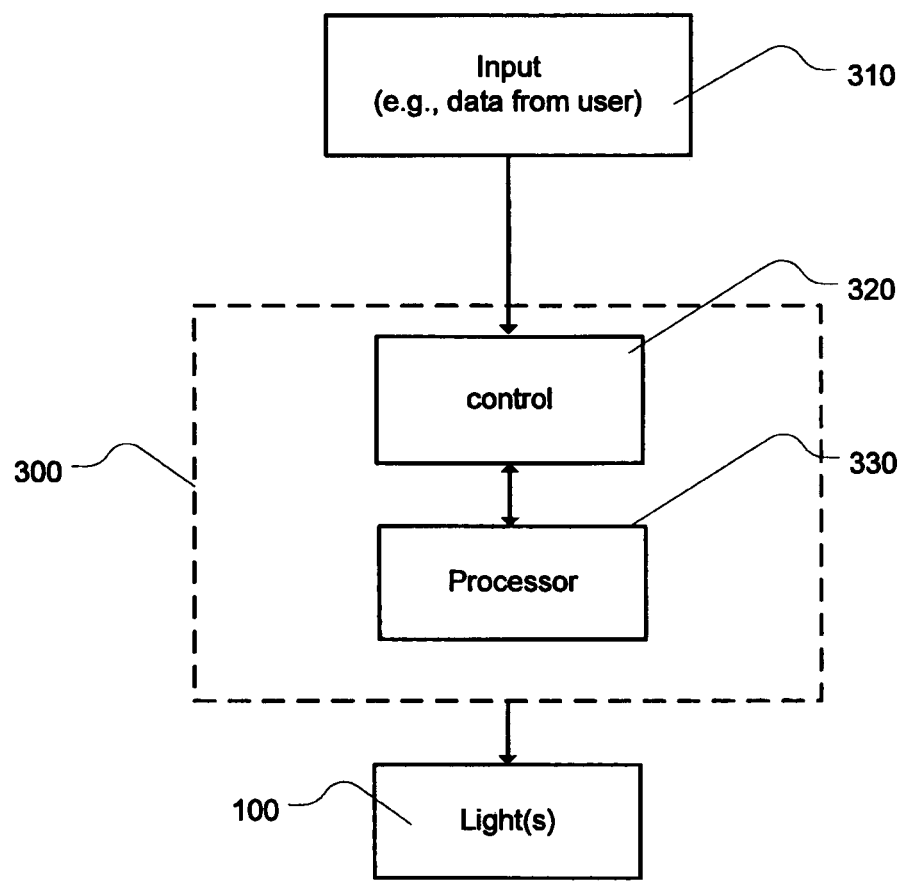
FIG. 2 is a process diagram according to the present technology.
Figure 3:
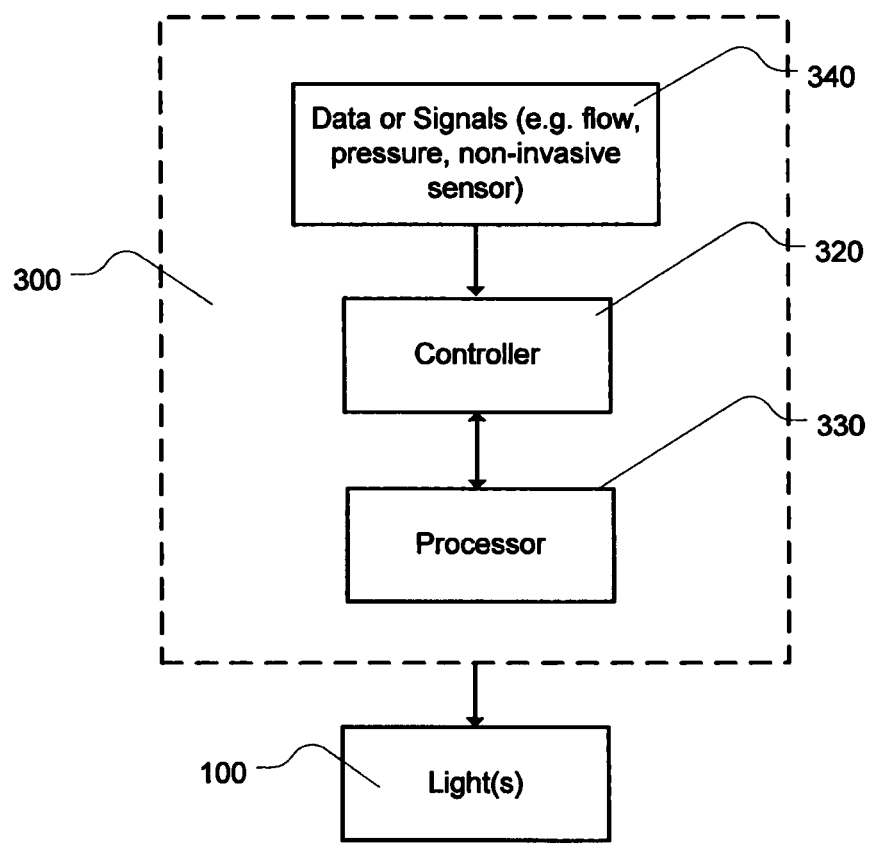
FIG. 3 is a process diagram according to the present technology.

FIGS. 2 and 3 are diagrams illustrating control relationships with the lights 100 and flow generator 300 in some embodiments of the present technology.

Lights 100 may be connected or triggered by a processor 330 in the flow generator 300. A control 320, such as an input interface, in the flow generator may deliver information to the processor 330, and the processor 320 may then trigger the lights 100 to turn on or off and may thereby provide a light therapy. Optionally, such operations may serve to adjust or vary an intensity of the output of the lights 100. For example, lights 100 may be controlled to change from an "off" state to a low intensity "on" state and then be controlled to gradually increase that intensity to a maximum intensity state over a preset time period. Still further, lights 100 may be controlled to gradually decrease intensity to an off state during a preset time period. Still further the processor may be configured to modify a color of the lights 100, such as by controlling selective varying of the intensity of different ones of a set of colored LEDs (e.g., red, green and blue LEDs). In some cases, the lights 100 may be controlled to flash as opposed to providing light therapy. Data settings for such time periods, intensities changes (e.g., max and min) and/or colors may optionally be entered via a user interface as discussed in more detail herein.

Lights 100 may be powered by flow generator 300. One or more wires or other means may connect the lights 100 to the flow generator 300 to power the lights and/or electrically communicate with the lights from the flow generator. Alternatively or in addition, a power cable may be positioned in a tube, for example a heated tube. Thus, the lights may be electrically coupled with a power line of the tube.

In an alternative, lights 100 may be powered independently of the flow generator, for example using batteries or solar power. The batteries may be stored on the mask 200, flow generator 300 or independently of the respiratory therapy system.

In an alternative, lights 100 may be powered using the heat generated by the flow generator or may optionally be powered by a small air turbine, such as a turbine generator located at an exhaust of the mask, that turns in response to air flow generated by the flow generator. In some such cases, the turbine may serve as a charger for a battery for the lights 100.

Time

Lights 100 may be turned on at a pre-determined or allocated time. For example, lights 100 may turn on at a time designated, set or input by the user on the flow generator, or may turn on at a time calculated by the processor 300 in the flow generator.

As shown in FIG. 2, the user may operate an input interface such as control 320 to enter data (e.g., input 310) into the flow generator 300 such as a display and/or buttons or via a programming device that is linked (e.g., wired or wirelessly) to the controller of the flow generator. The user may include the patient, their clinician or other person. The user may enter a time of day (e.g., 8 a.m.) for the lights 100 to be triggered or turned on or switched from a first state to a second state. The user may enter an amount of time (e.g., 6 hours) that they wish to receive therapy from the flow generator 300 before the light 100 turns on (e.g., the light 100 will turn on after 6 hours of positive air pressure therapy has been delivered.)

Alternatively, the flow generator 100 may calculate the amount of sleep the patient requires (e.g., 8 hours) or to determine the average number of hours the patient generally sleeps based on previous usage data. The apparatus may then automatically calculate (via the processor 330) the time the lights 100 are to be turned on or switched from a first state to a second state. The time may be calculated based on the start of the patient's therapy. For example, if that patient begins therapy at 10 pm, the flow generator 300 may calculate that the lights 100 are to be turned on or switched between a first state and a second state at 6 am. Optionally, a user may set a period of time for the operation of the lights to permit them to provide a light therapy during the selected period of time. The apparatus may then control the light to operate, such as at a generally constant therapy intensity, during the selected period of time.

Sleep State

Lights 100 may be turned on or switched between a first state and a second state according to the patient's sleep state. For example, lights 100 may turn on when the patient is in an awake state.

Sleep state may, for example, be determined by measuring respiratory characteristics, as disclosed in pending PCT application WO2011/006199, filed Jul. 14, 2010, which is incorporated by reference herein in its entirety. Other methodologies may be implemented by an apparatus for detection of sleep condition or sleep state in some embodiments of the present technology.

FIG. 3 shows an exemplary control relationship by which lights 100 may be activated. Data 340, or signals, which may include flow, pressure, and/or other respiratory characteristics, may be delivered to controller 320 in flow generator 300. Controller 320 may then send this information to processor 330 for calculating the patient's sleep state. The processor 330 may decide if the patient is in an awake state or a sleep state. If the patient is in a sleep state, the lights 100 may not be triggered. If the patient is in an awake state, lights 100 may be triggered and therefore illuminate.

Processor 330 may also determine if the patient is progressing towards an awake state. If this progression to an awake state is detected, lights 100 may be triggered to turn on gradually or ramp up to full illumination.

In a further alternative, processor 330 may determine if the patient is progressing from an awake state to a sleep state (for example at the beginning of their positive air pressure therapy). If this progression from an awake state to a sleep state is detected, lights 100 may be switched or transitioned from a first, on state, to a second, off state.

By way of further example, a processor, such as one of the flow generator, may be configured to determine how much time a user has slept in accordance with a detection of sleep state (e.g., REM sleep), such as by running a timer while a processor determines a patient is presently in a sleep state. Thus, the timer may represent an accumulated sleep time. When the accumulated sleep time exceeds a pre-set sleep time (e.g., 7.5 hours of sleep), the lights 100 may then be triggered by the processor. Such accumulated sleep time may exclude periods of time during which the processor detects that the patient's sleep has been disturbed or that the patient is awake (e.g., not yet fallen asleep).

In an example operation, the flow generator may be turned on for a night's sleep session. The processor may initially control the lights, such as for light therapy, to be in an on state at the beginning of the treatment session, and may optionally be maintained at a desired therapy intensity for a pre-set period of time. During another preset period of time, the lights may then be controlled by the processor to gradually decrease in intensity. Optionally, the gradual decrease may be interrupted and the lights may be immediately turned off if the processor detects that the patient has initially fallen asleep or entered a sleep state. During the treatment session the processor may determine an accumulated sleep time and trigger the lights to activate at a low intensity when the desired sleep time has been reached. The lights may then gradually increase in intensity during a pre-set period of time. However, if the processor detects that the patient has entered an awake state, the gradual increase in intensity may be interrupted and the lights may be set (e.g., immediately) to a full intensity or desired therapy intensity upon the detection of the awake state.

Environment Detection

In some embodiments of the present technology, an exemplary light therapy device may monitor or sense a patient's environment and control a delivery of light therapy, such as by activating the lights 100, or some other form of therapy in response to detecting one or more environmental conditions. For example, a patient may require a respiratory treatment apparatus, such as a ventilator or CPAP apparatus, which may itself optionally include a control panel with lights for light therapy generation and/or speakers for sound generation. However, the respiratory treatment apparatus may also interface, either wirelessly or via a wire bus or cable, with a control system of a discrete light therapy module. In such a case, the light therapy module may include a processor such as the example processor 330 as described herein and lights 300 for light therapy. The respiratory treatment apparatus may then communicate data detected by the respiratory treatment apparatus to the control system of the light therapy module, such as flow data, breath rate data, heart rate data, and/or sleep state data, sleep disordered breathing events (e.g., apnea, hypopnea, snoring) etc. In such a case, the light therapy module may control light and/or sound therapy based on data detected by and transmitted from the respiratory treatment apparatus. In some cases, the light therapy module may evaluate data from the respiratory treatment apparatus. and perform a sleep state analysis to detect sleep state within the module. Modularization of such a light therapy component may optionally be achieved as described in U.S. Provisional Patent Application No. 61/533,431, filed on Sep. 12, 2011, the entire disclosure of which is incorporated herein by reference.

In some embodiments, the light therapy module may itself include one or more sensors to monitor the patient's environment, including monitoring the medical equipment, such as respiratory treatment apparatus, as discussed above. In one example, an exemplary light therapy module may include one or more sensor(s). Such sensors may include, for example, a light sensor and/or sound sensor, to monitor any light or sound proximate to the patient, such as the light or sound produced by the medical equipment. In response to such environmental conditions detected with the sensor, the light therapy module may modify the patient's environment.

For example, an exemplary light therapy module may include a light sensor to monitor light conditions in a patient's environment. Such a sensor may be of any type capable of detecting light near the sensor, such as a charge-coupled device (CCD), an electro-optical sensor, photodetector, photodiode, fiber optic sensors, or any other similar sensor. An exemplary light therapy module may also include a sound sensor to monitor sound conditions in a patient's environment. Such a sensor may be of any type capable of detecting sound or a level of sound, such as a microphone or any other similar type of sensor. Optionally, the sensors may be coupled with a processor 330 of the module or of the flow generator.

With such sensors, the processor 330 may detect environmental conditions, such as light and/or sound conditions that may interfere with sleep. For example, the sound sensor may detect a sound level in the patient's environment that is greater than a predetermined sound threshold that may be considered to be disruptive. Such a disruptive sound threshold may be set by a user with a user interface. For example, the predetermined sound threshold may be a set decibel level such as 0 dB, 30 db, 80 db etc. In some embodiments, the processor with the sound sensor may also detect other aspects of the environment, including particular frequency, period, wavelength, or any other measurable characteristic of sound.

Similarly or alternatively, the light sensor may detect a light level, or illuminance, in the patient's environment which is greater than a predetermined threshold that may be considered to be disruptive. Such a disruptive light threshold may be set by a user with a user interface. For example, the predetermined light threshold may be a set illuminance level such as 0 lux, 50 lux etc. The processor with the light sensor may also detect other measurable characteristics of environmental light, such as frequency, period, wavelength, or any other measurable characteristic.

In some cases, the processor may thereafter control a change to the environment based on such detected conditions. For example, based on the detected sound and/or light, the processor of the light therapy module may control a generation of white noise with a speaker of the module to promote sleep. Optionally, the processor of the light therapy module may control a generation of noise cancelling sound (e.g., an inverted sound signal from the signal of the sound sensor) with one or more speakers. Similarly, based on the detection of sound, such as when a processor detects a sleep state for the patient, the processor may control a change to the lights of the module, the respiratory treatment apparatus and/or light 100 such as by reducing the light level(s).

Thus, based on data from the respiratory treatment apparatus and/or data gathered from the one or more sensors, the light therapy module or the respiratory treatment apparatus may control an adjustment to the lights or sounds or other form of therapy in response to the data or sensed conditions.

In another example, such a control system may receive data indicating that a patient is in need of rest (such as a patient activation of a sleep button or a detection that the patient has not slept for a preset sleep time). If a patient is in need of sleep, the control system may transmit instructions or otherwise control the lights, such as of the light therapy module, to modify the patient's environment in order to encourage sleep. Such modifications may take on various forms, depending on the personal preference of the patient or the detected conditions. For example, a processor may dim the lights of the respiratory treatment apparatus, mask or light therapy module. In some cases, a mask may be provided or implemented with controllable eye shades (e.g., electrochromic glass lenses or electromechanical shutters) such that the eye shades may be activated to shade the eyes from light so as to encourage sleep.

In some instances, the control system may receive data indicating that a patient is rested and must awaken, such as with a timer previously discussed. In such examples, the control system may issue instructions to the light therapy module to modify the patient's environment in order to encourage waking up. Such modifications may include actuating an environmental or therapy lighting system, such as the lights 100, to increase light level or sound level, or undoing any modifications previously made to encourage sleep, such as restoring a respiratory treatment apparatus control panel light level, deactivating eye shades, deactivating a white noise emitter or deactivating a noise canceling device.

Docking Station

Figure 5A:
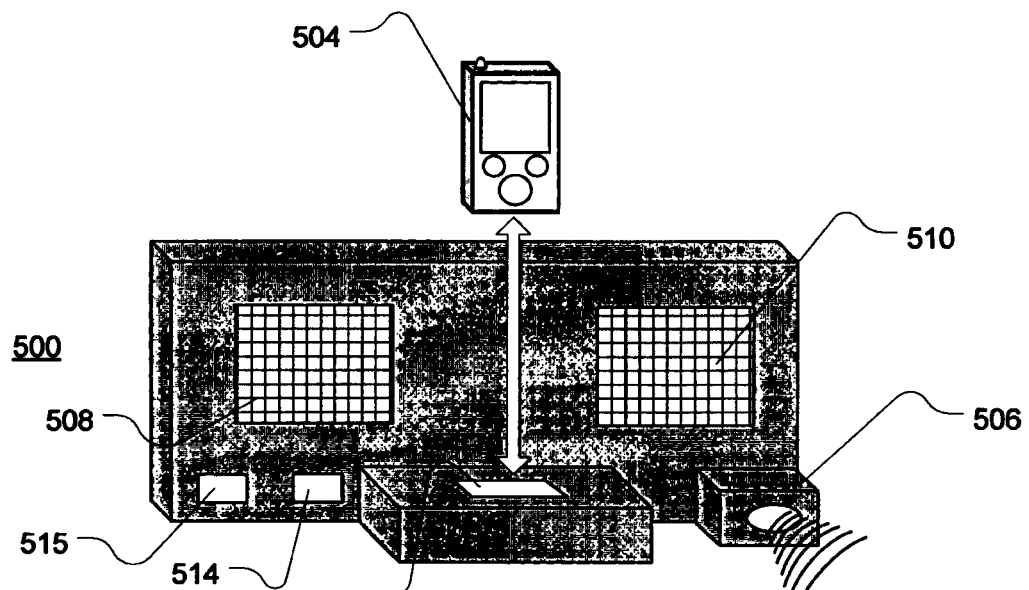
FIGS. 5A and 5B are perspective views illustrating a docking station for docking of a personal data assistant (PDA) or mobile computing device such as a mobile phone or tablet device in some embodiments.
Figure 5B:
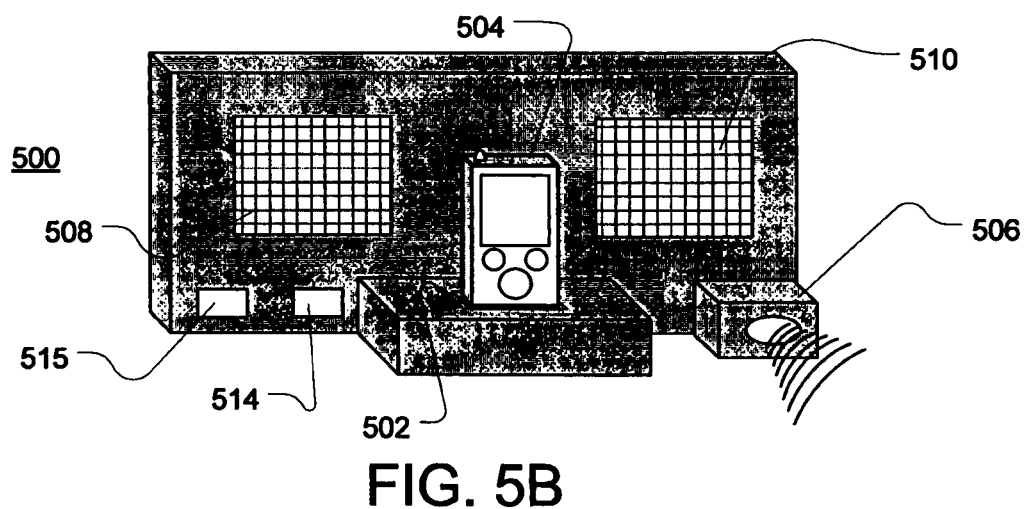

In some embodiments, the light therapy module may be implemented as a docking station. FIGS. 5A and 5B illustrate such an example docking station 500. The docking station 500 may include a connection interface 502 for communication with a mobile computing device 504 and may serve as a stand for the mobile computing device when inserted into a receptacle portion of the housing of the docking station. Mobile computing device may be any handheld device, such as a portable data assistant, mobile phone, tablet computer, that may be capable of any or all of the following: placing or receiving phone calls, connecting to a cellular network, connecting to a WiFi hotspot, sending or receiving text messages or emails, playing digital music, scheduling or calendar functions, or navigation. Connection interface 502 may be sized and dimensioned to receive such a mobile computing device 504 and may include any type of communication port capable of connection with mobile computing device 504. Docking station may also include an optional auxiliary input 514 for connecting any type of mobile computing device 504 which does not mate with connection interface 502, such as devices which connect by mini or micro USB connections, etc. A respiratory treatment apparatus communications interface port 515 may also be provided for communications with a controller of such a device. The docking station may also include one or more wireless transceivers that may serve as an interface for communications with such external devices.

Docking station 500 may also include sensors as previously mentioned, such as a sensor 506 adapted to monitor characteristics of a patient as discussed in more detail herein. Additionally, docking station 500 may include a speaker(s) 508 and/or light(s) 510.

The operations set by programmed algorithms as described herein may thus be implemented by one or more processors such as a processor of the docking station, a processor of the mobile computing device and a processor of the respiratory treatment apparatus. Such processors may collectively or individually serve as the control system for the therapies and operations described herein. For example, a light therapy application run by the processor of the mobile computing device (or a processor of the docking station) may detect a sleep state with signals of the sensor of the docking station (and/or signals from the sensors of the respiratory treatment apparatus) and send suitable signals to activate and deactivate lights as previously described (such as lights 100 and/or of docking station) to control a light therapy for the user of the respiratory treatment apparatus and/or of the docking station. In this regard, in some embodiments, both the lights of the docking station and the lights 100 may be synchronized to provide a complementary light therapy. Such synchronized therapy may optionally be activated by communications between a processor of the respiratory treatment apparatus and a processor of the docking station module with or without communications of a docked mobile computing device.

Figure 6:
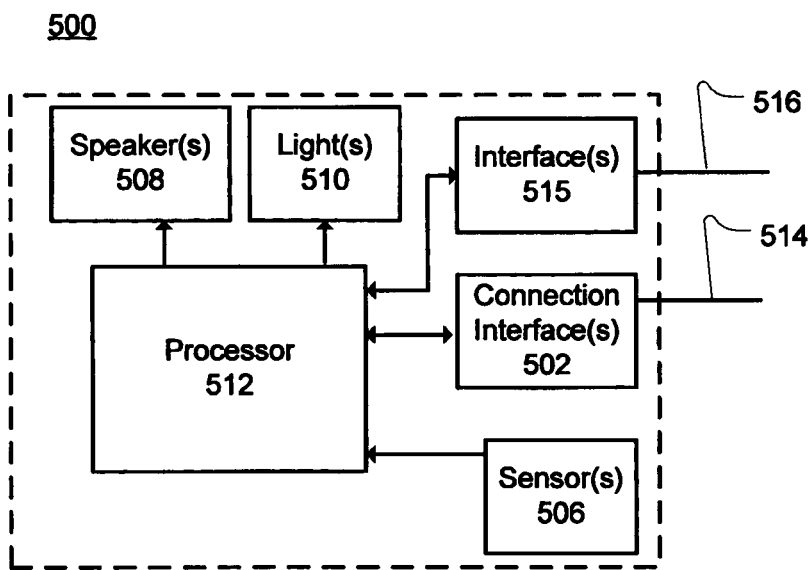
FIG. 6 is an example block diagram of some components of the docking station of FIG. 5.

A suitable configuration for some components of the docking station is further illustrated in FIG. 6. The components may include processor 512. Processor 512 may perform any or all of the methodologies of controller 320 and processor 330, as described herein, such as activating/deactivating the speakers 508 and/or lights 510.

Upon connection of a mobile computing device 504 to connection interface 502, processor 512 may begin communication with the mobile computing device 504. Thus, the processor 512 may receive instructions from mobile computing device 504, such as instructions to activate activate/deactivate speakers 508 and/or lights 510. Similarly, a processor of the mobile computing device may process and evaluate signals from the sensor 506.

Under control of a processor, such as processor 512 or processor of the mobile computing device, signals from the sensor 506 may be evaluated to monitor the sleep state of a patient. In response to a sleep state detected, a processor may trigger one or more of speakers 508 and/or lights 510. Sensor 506 may include a non-invasive bed side monitor such as the BiancaMed SleepMinder sensor which utilizes Doppler radar, as described in U.S. Patent Application Pub. NO. 2009-0203972, filed on Nov. 28, 2006, the disclosure of which is hereby incorporated by reference in its entirety.

As previously mentioned, docking system 500 may interface with a respiratory treatment apparatus, such as a positive airway pressure treatment apparatus. The respiratory treatment apparatus may connect to docking system by interface port 515 or may connect wirelessly through a network, Bluetooth, or any. other wired or wireless connection. Such a respiratory treatment apparatus may include a flow generator, such as flow generator 300 describe above. In one example, processor 512 may receive data from both sensor 506 and a processor of the respiratory treatment apparatus. The respiratory treatment apparatus may communicate patient data such as breath cycle, respiratory rate, cardiac rate, respiratory events (e.g., SDB events such as central and obstructive apneas, central and obstructive hypopneas, snoring) etc. to or from the dock. Optionally, these events of the patient data may also be detected by the processor 512 from the signals of the sensor 506. Thereafter, any of the processors of the system, upon receipt of the respective data, may compare the detected patient data, such as to confirm accuracy of the detections. Such a comparison may verify the operation of both sensor 506 and/or respiratory treatment apparatus.

In another similar example, where sensors are not operational, such as sensor 506 or sensors of the respiratory treatment apparatus, data from the operating sensor may serve as a back-up for the other non-operational sensor to permit continued operation of the apparatus that lacks the working sensor.

Aroma Therapy

In some embodiments, a conduit of the air delivery pathway of the system, such as in the mask or in flow generator, may include one or more aroma release chambers with suitable mechanisms for activation of each. For example, an aroma cartridge may be a replaceable component of a flow chamber or pathway that may include a mechanical shutter or an electromechanical valve that selectively permits or prevents air flow of the system to traverse through the aroma cartridge. By such a process, each mechanism may selectively permit the activated flow to go through a cartridge to release an aromatic substance of the cartridge. For example, each mechanism may be controlled to open or close by a control signal generated by the controller or processor of the flow generator. The aroma may then be directed to a user of the apparatus via the mask by an airflow pathway from cartridge. Different control methodologies of the aroma's release may then be controlled or timed by a processor with one or more different aroma cartridges.

For example, in order to influence circadian phase, aromas may be chosen and their release controlled to promote sleep and/or promote wakefulness in the patient at suitable or desired times. For example, an awake aroma cartridge (e.g., a coffee scent or ground coffee, peppermint, cinnamon, etc.) of an awake scent chamber may be activated into the airflow at a time or timing suitable for a patient to be awake, such as in conjunction with any of the light control activation methodologies previously discussed. Similarly, a relaxing or sleep aroma cartridge of a sleep scent chamber, such as a cartridge having a scented oil such as lavender, marjoram, geranium, mandarin, and/or cardamom etc., may be activated into the airflow at a time or timing suitable for a patient to be or fall asleep, such as in conjunction with any of the light control de-activation methodologies previously discussed or at a preset time suitable for patient sleep. By such control over therapy scent and/or therapy light, a patient's circadian phase of the patient may be influenced by the apparatus.

Further Examples

In a further alternative, the flow generator may measure a patient respiratory characteristic and modify a parameter of the light therapy device based on the patient respiratory characteristic.

In a further alternative, the light therapy may be delivered to the patient and the flow generator may measure a patient response to the light therapy, and subsequently modify a parameter of the respiratory therapy device or flow generator based on the patient response to the light therapy.

In a further alternative, the brightness of the light may be modified or changed depending on a patient respiratory characteristic. For example, the light may be constantly on, and the brightness of the light may be dimmed or illuminated depending on the patient respiratory characteristic.

Advantages of Some Examples of the Present Technology

Types of sleep disorders may include Seasonal Affective Disorder (SAD), and Circadian Rhythm Sleep Disorders (CRSD). Melatonin production in these patients causes them to be sleepy at time when they need to be awake. Light therapy can assist in reducing melatonin production therefore transitioning the patients from sleep to awake.

The light passes through the retinohypothalmic tract, which is the connection between the eyes and the hypothalamus and causes the central nervous system to send signals to the pineal gland to suppress the secretion of melatonin.

Light therapy can also involve placing a light source 1-3 feet away from the patient. The light can be emitted from multiple fluorescent tubes at intensities ranging from 2500-12000 lux. The light may be distributed evenly using a diffusion screen over the tubes, and this also may serve to prevent UV wavelengths from getting through. The retina is more sensitive to light, so the light may be positioned overhead, coming down over the eyes.

SAD can affect some patient's living in areas where the days are shorter and the nights are longer, for example in winter. These patients may suffer changes in mood, energy and appetite.

CRSD affects people who cannot sleep and wake at normal times because their circadian rhythm is abnormal. There are two forms of CRSD—extrinsic and intrinsic. Extrinsic CRSD is caused by circumstance, for example due to shift work or jet lag. Intrinsic CRSD is where the body's internal clock is different to that of the patient's surroundings. Intrinsic CRSD includes Delayed Sleep Phase Syndrome (DSPS) where the body has an urge to sleep later at night with a peak alertness in the middle of the night, and Advanced Sleep Phase Syndrome (ASPS) where the body is more alert during the night and asleep in the morning.

Light therapy can be administered either early in the morning (for treating SAD or DSPS) or late at night (ASPS or extrinsic CRSD).

There may be a number of patients being treated for SDB with respiratory therapy or positive air pressure treatment. These patients are utilizing these respiratory therapies at least late at night and early in the morning. An advantage of the present technology is that some embodiments of the technology may facilitate the combination of positive air pressure treatment and light therapy for the treatment of, for example, sleep disorders including: SDB, SAD and/or CRSD. The proximity of the mask to the patient's eyes facilitates treatment of various sleep disorders simultaneously and synergistically. Furthermore, since the flow generator or ventilator is monitoring patient data such as start of sleep time, sleep duration, sleep quality, sleep state, and various other parameters, it is possible to synchronize the light therapy with respiratory therapy.

This may have many benefits to the patient, including: more effective light therapy treatment as the sleep cycle is indicative of the patient's circadian rhythm; convenience as both disorders can be treated simultaneously and synergistically; and efficient use of patient data because the light therapy system and the respiratory therapy system can utilize the same patient data therefore eliminating the need for two independent systems.

Moreover, an apparatus with such features configured to influence circadian rhythm may be implemented for the treatment of patients who may suffer myocardial infarction. For example, for patients who may suffer from myocardial infarction at a typical or non-random time, timing of the therapies of the example apparatus described herein may be set with a controller so as to be activated at times that shift the circadian rhythm of such patients. Such treatment, e.g., sound, aroma and/or light therapy, may thereby serve to reduce the occurrence of myocardial infarction.

As discussed herein, the controller or processor(s) can be configured to implement the control methodologies such as the algorithms described in more detail herein. Thus, the controller or processor may include integrated chips, a memory and/or other control instruction, data or information storage medium. For example, programmed instructions encompassing such a control methodology may be coded on integrated chips in the memory of the device(s). Such instructions may also or alternatively be loaded as software or firmware using an appropriate data storage medium. With such a controller or processor, the device(s) can be used for determining and analyzing many different respiratory, sound and light related parameters, based on data or signals from the sensors.

While the technology has been described in connection with what are presently considered to be the most practical and preferred embodiments, it is to be understood that the technology is not to be limited to the disclosed embodiments, but on the contrary, is intended to cover various modifications and equivalent arrangements included within the spirit and scope of the disclosure. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

The invention claimed is:

1. A respiratory therapy system for treating a patient with a sleep disorder, comprising:
  a mask adapted to sealingly engage with the respiratory system of a patient, the mask including a forehead support comprising a forehead support beam connected to a forehead support pad configured to rest on the patient's forehead;
  a flow generator adapted to deliver pressurized breathable gas to the mask; and
  a therapy light having an off state and an on state;
  wherein the therapy light is located on the mask and is in electrical communication with the flow generator, and the flow generator is configured to switch the light between the off state to the on state if the flow generator detects a condition, the therapy light configured on the forehead support of the mask so that a user can see beyond the mask while wearing the mask in use.

2. A system for treating sleep apnea according to claim 1, wherein the condition is a predetermined time.

3. A system for treating sleep apnea according to claim 2, wherein the predetermined time is an input from a user.

4. A system for treating sleep apnea according to claim 1, wherein the condition is a sleep state.

5. A system for treating sleep apnea according to claim 4, wherein the sleep state is an awake state.

6. A system for treating sleep apnea according to claim 4, wherein the light gradually adjusts from an off state to an on state when the patient is transitioning from sleep state to awake state.

7. A system for treating sleep apnea according to claim 4, wherein the light gradually adjusts from an on state to an off state when the patient is transitioning from awake to sleep state.

8. A system for treating sleep apnea according to claim 4 wherein the therapy light is coupled at a portion of the mask.

9. A system for treating sleep apnea according to claim 1 further comprising an aroma chamber, wherein the flow generator is configured to selectively activate gas flow through the aroma chamber to selectively release an aroma from the chamber to a breathable gas of the mask.

10. A system for treating sleep apnea according to claim 9 wherein the aroma chamber, comprises a replaceable aroma cartridge.

11. The respiratory therapy system of claim 1 wherein the light is located on the forehead support beam.

12. The respiratory therapy system of claim 1 further comprising a therapy light located on the flow generator.

13. The respiratory therapy system of claim 1 wherein the light is located on the forehead support pad.

14. The respiratory therapy system of claim 1 wherein the light is configured on the mask to permit a releasable attachment of the light from the mask.

15. The respiratory system of claim 1 wherein the light is attached to the forehead support by a flexible wire.

16. The respiratory therapy system of claim 1 wherein, in use, position of the light is adjustable so as to selectively direct or shield the light.

17. The respiratory therapy system of claim 1 wherein, in use, the light is positioned overhead, its emitted light coming in a downward trajectory to the patient's eyes.

18. The system of claim 1 wherein the flow generator is configured to activate the therapy light during delivery of the pressurized breathable gas to the mask.

19. A therapy system comprising:
   a mask adapted to sealingly engage with the respiratory system of a patient and configured to receive a flow of air from a respiratory device;
   a light located on the mask; and
   a controller, including at least one processor, the controller configured to set a light therapy operation of the light, the light configured on a forehead support beam of the mask so that a user can see beyond the mask while wearing the mask in use.

20. The therapy system of claim 19, wherein the controller is configured to switch the light between an off state to an on state if the controller detects a condition, wherein the condition is a predetermined time.

21. The therapy system of claim 20, wherein the predetermined time is an input from a user.

22. The therapy system of claim 19, wherein the controller is configured to switch the light between an off state to an on state if the controller detects a condition, wherein the condition is a sleep state.

23. The therapy system claim 22, wherein the sleep state is an awake state.

24. The therapy system of claim 22, wherein the light gradually adjusts from an off state to an on state when the patient is transitioning from sleep state to awake state.

25. The therapy system of claim 22, wherein the light gradually adjusts from an on state to an off state when the patient is transitioning from awake to sleep state.

26. The therapy system of claim 19 further comprising an aroma chamber, wherein the respiratory device is configured to selectively activate gas flow through the aroma chamber to selectively release an aroma from the chamber to a breathable gas of the mask.

27. The therapy system of claim 26 wherein the aroma chamber, comprises a replaceable aroma cartridge.

28. The therapy system of claim 19 further comprising a light sensor.

29. The therapy system of claim 28 wherein a processor of the system detects a level of light and controls a change of an intensity of the light in response to light detected by the sensor.

30. The therapy system of claim 19 further comprising a sound sensor and a speaker.

31. The therapy system of claim 30 wherein a processor of the system detects a level of sound and controls a generation of a sound signal in response to sound detected by the sensor.

32. The system of claim 19 wherein the controller is configured to activate the therapy light during delivery of the flow of air from the respiratory device.

33. A respiratory therapy system comprising:
   a mask adapted to sealingly engage with the respiratory system of a patient;
   a flow generator adapted to deliver pressurized breathable gas to the mask; and
   a therapy light having an off state and an on state;
   wherein the therapy light is located on the mask and is in electrical communication with the flow generator, and the flow generator is configured to switch the therapy light between the off state to the on state if the flow generator detects a condition, the therapy light configured for attachment to the mask so that a user can see beyond the mask while wearing the mask in use.

34. The respiratory therapy system of claim 33, wherein the mask includes a frame and wherein the therapy light is located on the frame.

35. The respiratory therapy system of claim 33, wherein the mask includes a cushion configured to sealingly engage with the face of the patient and wherein the therapy light is located on the cushion.

36. The respiratory therapy system of claim 33, wherein the therapy light includes an attachment component to secure the therapy light to the mask.

37. The respiratory therapy system of claim 33, wherein the mask includes a forehead support proximate to the patient's forehead and the therapy light is located on the forehead support.

38. The respiratory therapy system of claim 33, wherein the condition is a predetermined time.

39. The respiratory therapy system of claim 38, wherein the predetermined time is an input from a user.

40. The respiratory therapy system of claim 33, wherein the condition is a sleep state.

41. The respiratory therapy system claim 40, wherein the sleep state is an awake state.

42. The respiratory therapy system of claim 40, wherein the light gradually adjusts from an off state to an on state when the patient is transitioning from sleep state to awake state.

43. The respiratory therapy system of claim 40, wherein the light gradually adjusts from an on state to an off state when the patient is transitioning from awake to sleep state.

44. The respiratory therapy system of claim 33 further comprising an aroma chamber, wherein the flow generator is configured to selectively activate gas flow through the aroma chamber to selectively release an aroma from the chamber to a breathable gas of the mask.

45. The respiratory therapy system of claim 44 wherein the aroma chamber, comprises a replaceable aroma cartridge.

46. The respiratory therapy system of claim 33 further comprising a light sensor.

47. The respiratory therapy system of claim 46 wherein a processor of the system detects a level of light and controls a change of an intensity of the light in response to light detected by the sensor.

48. The respiratory therapy system of claim 33 further comprising a sound sensor and a speaker.

49. The respiratory therapy system of claim 48 wherein a processor of the system detects a level of sound and controls a generation of a sound signal in response to sound detected by the sensor.

50. The system of claim 33 wherein the flow generator is configured to activate the therapy light during delivery of the pressurized breathable gas to the mask.

* * * * *